(12) United States Patent
Haddock et al.

(10) Patent No.: US 9,125,902 B2
(45) Date of Patent: Sep. 8, 2015

(54) METHODS FOR TREATING AN INTERVERTEBRAL DISC USING LOCAL ANALGESICS

(75) Inventors: Sean M. Haddock, Memphis, TN (US); Susan J. Drapeau, Cordova, TN (US); Thomas Andrew Simonton, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 788 days.

(21) Appl. No.: 12/695,888

(22) Filed: Jan. 28, 2010

(65) Prior Publication Data

US 2011/0184037 A1    Jul. 28, 2011

(51) Int. Cl.
| | | |
|---|---|---|
| A61K 31/30 | (2006.01) | |
| A61K 31/4168 | (2006.01) | |
| A61K 47/32 | (2006.01) | |
| A61K 9/00 | (2006.01) | |
| A61K 47/34 | (2006.01) | |

(52) U.S. Cl.
CPC .......... *A61K 31/4168* (2013.01); *A61K 9/0024* (2013.01); *A61K 47/34* (2013.01)

(58) Field of Classification Search
USPC .................................. 514/401, 772.7, 772.4
See application file for complete search history.

(56) References Cited

U.S. PATENT DOCUMENTS

| | | | |
|---|---|---|---|
| 4,624,255 A | 11/1986 | Schenck et al. | |
| 4,742,054 A | 5/1988 | Naftchi | |
| 4,863,457 A | 9/1989 | Lee | |
| 5,522,844 A | 6/1996 | Johnson | |
| 5,571,882 A | 11/1996 | Vetter | |
| 5,626,838 A | 5/1997 | Cavanaugh, Jr. | |
| 5,759,583 A | 6/1998 | Iwamoto et al. | |
| 5,868,789 A | 2/1999 | Huebner | |
| 5,942,241 A | 8/1999 | Chasin et al. | |
| 6,069,129 A | 5/2000 | Sandberg et al. | |
| 6,123,731 A | 9/2000 | Boyce et al. | |
| 6,179,862 B1 | 1/2001 | Sawhney | |
| 6,248,345 B1 | 6/2001 | Goldenheim et al. | |
| 6,287,588 B1 | 9/2001 | Shih et al. | |
| 6,326,020 B1 | 12/2001 | Kohane et al. | |
| 6,331,311 B1 | 12/2001 | Brodbeck et al. | |
| 6,428,804 B1 | 8/2002 | Suzuki et al. | |
| 6,440,444 B2 | 8/2002 | Boyce et al. | |
| 6,461,631 B1 | 10/2002 | Dunn et al. | |
| 6,524,607 B1 | 2/2003 | Goldenheim et al. | |
| 6,534,081 B2 | 3/2003 | Goldenheim et al. | |
| 6,589,549 B2 | 7/2003 | Shih et al. | |
| 6,616,946 B1 | 9/2003 | Meier et al. | |
| 6,630,155 B1 | 10/2003 | Chandrashekar et al. | |
| 6,632,457 B1 | 10/2003 | Sawhney | |
| 6,652,883 B2 | 11/2003 | Goupil et al. | |
| 6,676,971 B1 | 1/2004 | Goupil et al. | |
| 6,696,073 B2 | 2/2004 | Boyce et al. | |
| 6,710,126 B1 | 3/2004 | Hirt et al. | |
| 6,723,741 B2 | 4/2004 | Jeon et al. | |
| 6,723,814 B2 | 4/2004 | Meier et al. | |
| 6,756,058 B2 | 6/2004 | Brubaker et al. | |
| 6,773,714 B2 | 8/2004 | Dunn et al. | |
| 6,843,807 B1 | 1/2005 | Boyce et al. | |
| 6,863,694 B1 | 3/2005 | Boyce et al. | |
| 6,921,541 B2 | 7/2005 | Chasin et al. | |
| 6,974,462 B2 | 12/2005 | Sater | |
| 7,045,141 B2 | 5/2006 | Merboth et al. | |
| 7,070,809 B2 | 7/2006 | Goupil et al. | |
| 7,144,412 B2 | 12/2006 | Wolf et al. | |
| 7,166,570 B2 | 1/2007 | Hunter et al. | |
| 7,220,281 B2 | 5/2007 | Lambrecht et al. | |
| 7,229,441 B2 | 6/2007 | Trieu et al. | |
| 7,235,043 B2 | 6/2007 | Gellman et al. | |
| 7,287,983 B2 | 10/2007 | Ilan | |
| 7,318,840 B2 | 1/2008 | McKay | |
| 7,329,259 B2 | 2/2008 | Cragg | |
| 7,361,168 B2 | 4/2008 | Makower et al. | |
| 7,367,978 B2 | 5/2008 | Drewry et al. | |
| 7,658,765 B2 | 2/2010 | Lambrecht et al. | |
| 2002/0009454 A1 | 1/2002 | Boone et al. | |
| 2002/0090398 A1 | 7/2002 | Dunn et al. | |
| 2002/0122771 A1 | 9/2002 | Holland et al. | |
| 2003/0022927 A1 | 1/2003 | Jeon et al. | |
| 2003/0185873 A1 | 10/2003 | Chasin et al. | |
| 2003/0204191 A1 | 10/2003 | Sater et al. | |

(Continued)

FOREIGN PATENT DOCUMENTS

| | | |
|---|---|---|
| WO | 03005961 A2 | 1/2003 |
| WO | 2005034998 A2 | 4/2005 |

(Continued)

OTHER PUBLICATIONS

Mirzai et al.; "Perioperative Use of Corticosteroid and Bupivacain Combination in Lumbar Disc Surgery: A Randomized Controlled Trial"; 2002; Spine; 27: 343-346.*

Atrigel, QTL, Inc. Drug Delivery Platform, Jul. 2006 revision,QTL USA, Inc. Fort Collins, CO.

Daniel P. Moore, M.D.; Helping your patients with spasticity reach maximal function, Aug. 1998, pp. 1-9, vol. 104, No. 2. http://www.postgraduate.com/issue/1998/08_98/moore,htm.

Kyphon, Enhanced Discyphor Catheter System, Kyphon Inc. 2007, Sunnyvale, CA.

*Primary Examiner* — Shirley V Gembeh

(74) *Attorney, Agent, or Firm* — Sorell Lenna & Schmidt LLP

(57) ABSTRACT

Effective methods of treating back pain from an intervertebral disc are provided. The methods of treatment include administering an immediate release analgesic at or near the intervertebral disc; administering a bulking agent or sealing agent within the intervertebral disc; and administering a sustained release analgesic within the intervertebral disc, wherein the sustained release analgesic releases the analgesic over a period of at least one day.

20 Claims, No Drawings

(56) References Cited

U.S. PATENT DOCUMENTS

| | | |
|---|---|---|
| 2003/0224033 A1 | 12/2003 | Li et al. |
| 2004/0072799 A1 | 4/2004 | Li et al. |
| 2004/0082540 A1 | 4/2004 | Hermida Ochoa |
| 2004/0109893 A1 | 6/2004 | Chen et al. |
| 2004/0214793 A1 | 10/2004 | Hermida Ochoa |
| 2005/0031666 A1* | 2/2005 | Trieu .................. 424/426 |
| 2005/0059744 A1 | 3/2005 | Donello et al. |
| 2005/0129656 A1 | 6/2005 | Goupil et al. |
| 2005/0142163 A1 | 6/2005 | Hunter et al. |
| 2005/0175709 A1 | 8/2005 | Baty, III et al. |
| 2005/0186261 A1 | 8/2005 | Avelar et al. |
| 2005/0197293 A1 | 9/2005 | Mellis et al. |
| 2005/0222684 A1 | 10/2005 | Ferree |
| 2005/0240269 A1 | 10/2005 | Lambrecht et al. |
| 2005/0287218 A1 | 12/2005 | Chaouk et al. |
| 2005/0288789 A1 | 12/2005 | Chaouk et al. |
| 2006/0030948 A1 | 2/2006 | Manrique et al. |
| 2006/0074422 A1 | 4/2006 | Story et al. |
| 2006/0106361 A1 | 5/2006 | Muni et al. |
| 2006/0148903 A1 | 7/2006 | Burch et al. |
| 2006/0183786 A1 | 8/2006 | Wang |
| 2006/0188583 A1* | 8/2006 | Lim et al. .................. 424/490 |
| 2006/0189944 A1 | 8/2006 | Campbell et al. |
| 2006/0228391 A1 | 10/2006 | Seyedin et al. |
| 2007/0004790 A1 | 1/2007 | Chow et al. |
| 2007/0093907 A1 | 4/2007 | Goupil et al. |
| 2007/0150061 A1 | 6/2007 | Trieu |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2008/0021074 A1 | 1/2008 | Cartt |
| 2008/0058953 A1 | 3/2008 | Scarborough |
| 2008/0091207 A1 | 4/2008 | Truckai et al. |
| 2008/0097229 A1 | 4/2008 | Roy et al. |
| 2008/0188945 A1 | 8/2008 | Boyce et al. |
| 2008/0269717 A1 | 10/2008 | Crandall et al. |
| 2009/0020076 A1 | 1/2009 | Ghiraldi |
| 2009/0155378 A1 | 6/2009 | Behnam et al. |
| 2009/0222096 A1 | 9/2009 | Trieu |
| 2009/0263489 A1 | 10/2009 | Zanella |
| 2009/0264489 A1 | 10/2009 | Hildebrand et al. |
| 2009/0275913 A1 | 11/2009 | Trieu |

FOREIGN PATENT DOCUMENTS

| | | |
|---|---|---|
| WO | 2007005177 A1 | 1/2007 |
| WO | WO 2009/129148 | * 10/2009 |

* cited by examiner

METHODS FOR TREATING AN INTERVERTEBRAL DISC USING LOCAL ANALGESICS

BACKGROUND

In human anatomy, the spine is a generally flexible column that can take tensile and compressive loads. The spine also allows bending motion and provides a place of attachment for muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

The intervertebral disc functions to stabilize the spine and to distribute forces between vertebral bodies. The intervertebral disc is composed of three structures: the nucleus pulposus, the annulus fibrosis, and two vertebral end plates. These components work to absorb the shock, stress, and motion imparted to the human vertebrae. The nucleus pulposus is an amorphous hydrogel with the capacity to bind water. The nucleus pulposus is maintained within the center of an intervertebral disc by the annulus fibrosis, which is composed of highly structured collagen fibers. The vertebral end plates, composed of hyaline cartilage, separate the disc from adjacent vertebral bodies and act as a transition zone between the hard vertebral bodies and the soft disc.

Intervertebral discs may be displaced or damaged due to trauma or disease. Disruption of the annulus fibrosis may allow the nucleus pulposus to protrude into the vertebral canal, a condition commonly referred to as a herniated or ruptured disc. The extruded nucleus pulposus may press on a spinal nerve, which may result in nerve damage, back pain, numbness, muscle weakness, and, in severe cases, paralysis. Intervertebral discs may also deteriorate due to the normal aging process. As a disc dehydrates and hardens, the disc space height will be reduced, leading to instability of the spine, decreased mobility and back pain.

One way to relieve the symptoms of these conditions is by surgical removal of a portion or the entire intervertebral disc. The removal of the damaged or unhealthy disc may allow the disc space to collapse, which would lead to instability of the spine, abnormal joint mechanics, nerve damage, as well as severe back pain. Therefore, after removal of the disc, adjacent vertebrae are typically fused to preserve the disc space. Spinal fusion involves inflexibly connecting adjacent vertebrae through the use of bone grafts or metals rods. Because the fused adjacent vertebrae are prevented from moving relative to one another, the vertebrae no longer rub against each other in the area of the damaged intervertebral disc and the likelihood of continued pain and inflammation is reduced. Spinal fusion, however, is disadvantageous because it restricts the patient's mobility by reducing the spine's flexibility, and it is a relatively invasive procedure.

Attempts to overcome these problems have led researchers to investigate the efficacy of implanting an artificial intervertebral disc to replace, completely or partially, the patient's damaged intervertebral disc. Disc replacement surgery generally involves removing the disc or damaged portion thereof and placement of an artificial disc in the evacuated disc space. Some desirable attributes of a hypothetical implantable disc include axial compressibility for shock absorbance, excellent durability to avoid future replacement, minimally invasive placement of the artificial disc to reduce post-operative discomfort, and biocompatibility. Existing artificial intervertebral discs include, for example, mechanically based (e.g. comprising rotational surfaces or springs), polymer based, and biopolymer based artificial discs.

Other attempts have focused on restoring disc height in, for example, a dehydrated intervertebral disc, where a portion or all of the nucleus pulposus and a prosthetic nucleus device is implanted in the intervertebral disc space to augment or completely replace the dehydrated nucleus. Alternatively, a total disc replacement operation may be performed wherein not just the dehydrated nucleus but the entire intervertebral disc is removed and replaced with a prosthesis. However, these types of treatment often involve complex surgery and inflict a good deal of trauma on the patient, resulting in increased post-surgical recovery times and disability.

Thus, there is a need to develop new methods of intervertebral disc treatments that reduce or prevent pain and/or inflammation associated with a damaged intervertebral disc.

SUMMARY

New methods of intervertebral disc treatments are provided that reduce or prevent pain and/or inflammation associated with a damaged intervertebral disc that cause back pain. By the administration of a local analgesic, a bulking agent or sealing agent and a sustained release analgesic at or near a damaged disc, pain and/or inflammation can be reduced or prevented.

In one embodiment, a method is provided for treating pain from an intervertebral disc in a patient in need of such treatment, the method comprising administering an immediate release analgesic at or near the intervertebral disc; administering a bulking agent or sealing agent within the intervertebral disc; and administering a sustained release analgesic within the intervertebral disc, wherein the sustained release analgesic releases the analgesic over a period of at least one day.

In another embodiment, there is a method of augmenting a nucleus pulposus within an annulus fibrosis in a patient in need of such treatment, the method comprising administering an immediate release analgesic at or near the annulus fibrosis; administering a bulking agent or sealing agent in the nucleus pulposus; and administering a sustained release analgesic within the annulus fibrosis or nucleus pulposus, wherein the sustained release analgesic releases the analgesic over a period of at least one day.

In yet another embodiment, there is a method for treating an intervertebral disc having a nucleus pulposus and an annulus fibrosis, the method comprising administering an immediate release analgesic at or near the annulus fibrosis; administering a bulking agent or sealing agent into the intervertebral disc space without removing nucleus pulposus or annulus fibrosis material; and administering a sustained release analgesic into the intervertebral disc, wherein the sustained release analgesic releases the analgesic over a period of at least three days.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

"Analgesic" refers to an agent or compound that can reduce, relieve or eliminate pain. Examples of analgesic agents include but are not limited to acetaminophen, a local anesthetic, such as for example, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof. Analgesic agents also include those with analgesic and anti-inflammatory properties, such as, for example, amitriptyline, carbamazepine, gabapentin, pregabalin, clonidine, or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to a drug (e.g., an anti-inflammatory agent, analgesic, or the like) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

"Treating" or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of the effective dosages of at least one analgesic agent may be used to prevent, treat or relieve the symptoms of pain.

"Localized" delivery includes delivery where one or more drugs are deposited within a tissue, for example, an intervertebral disc, a nucleus pulposus, an annulus fibrosis, or in close proximity (within about 5 cm, or preferably within about 2 cm, for example) thereto. A "targeted delivery system" provides delivery of one or more drugs depots having a quantity of therapeutic agent that can be deposited at or near the target site as needed for treatment of pain, inflammation or other disease or condition.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

Drug Depot

New methods of intervertebral disc treatments are provided that reduce or prevent pain and/or inflammation associated with a damaged intervertebral disc that causes back pain. By the administration of a local analgesic, a bulking agent or sealing agent and a sustained released analgesic at or near a damaged disc, pain and/or inflammation can be reduced or prevented.

In one embodiment, a method is provided for treating pain from an intervertebral disc in a patient in need of such treatment, the method comprising administering an immediate release analgesic at or near the intervertebral disc; administering a bulking agent or sealing agent within the intervertebral disc; and administering a sustained release analgesic within the intervertebral disc, wherein the sustained release analgesic releases the analgesic over a period of at least one day. The immediate release analgesic and/or sustained release analgesic can be administered in the form of a drug depot.

A "drug depot" comprises the composition in which at least one active pharmaceutical ingredient or drug is administered to the body. Thus, a drug depot may comprise a physical structure to facilitate implantation and retention in a desired site (e.g., a disc space, a spinal canal, a tissue of the patient, particularly at or near a site of surgery, pain, or site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least one anti-inflammatory agent or its pharmaceutically acceptable salt and/or at least one analgesic agent or its pharmaceutically acceptable salt.

A "depot" includes but is not limited to capsules, coatings, matrices, wafers, sheets, strips, ribbons, pills, pellets, microspheres, or other pharmaceutical delivery system or a combination thereof. Suitable materials for the depot are ideally pharmaceutically acceptable biodegradable and/or any bioabsorbable materials that are preferably FDA approved or GRAS materials. These materials can be polymeric or nonpolymeric, as well as synthetic or naturally occurring, or a combination thereof. Typically, the depot will be a solid or semi-solid formulation comprising a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

Suitable drug depots useful in the present application are described in U.S. Ser. No. 12/105,474 filed Apr. 18, 2008 and published as U.S. Publication No. 20090263489, and U.S. Ser. No. 12/396,122, filed Mar. 2, 2009 and published as US20090263459. The entire disclosure of these applications is incorporated by reference herein in their entirety.

The drug depot comprises a therapeutically effective amount of the analgesic. A "therapeutically effective amount" or "effective amount" is such that when administered, the drug results in alteration of the biological activity, such as, for example, inhibition of inflammation, reduction or alleviation of pain, improvement in the condition through muscle relaxation, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation of the drug depot is designed for immediate release. In other embodiments the formulation is designed for sustained release. In other embodiments, the formulation comprises one or more immediate release surfaces and one or more sustain release surfaces.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, pellets, microparticles, microspheres, microcapsules, spheroids, shaped derivatives and paste. Further, the formulations may be used in conjunction with any implantable, or insertable system that a person of ordinary skill would appreciate as useful in connection with embodiments herein including but not limited to parenteral formulations, microcapsules, pastes, implantable rods, pellets, plates or fibers, etc.

The immediate release analgesic is administered first. The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1, 2, 3, 4, 5, 6, 7, 8, 9, 10, 11, or 12 hours. The immediate release formulation provides relief of pain from the diagnostic and/or therapeutic procedure. For example, if the patient is going for a diagnostic procedure such as a discogram, the patient can receive a local immediate release analgesic at or near the damaged disc that provides pain relief so the procedure can be performed. If more pain control is needed, the patient can receive local delivery of a sustain release analgesic agent that can provide pain relief for extended periods of time (e.g., greater than 24 hours).

In another example, if the patient is going for a therapeutic procedure such as a discectomy or a disc decompression, the patient can receive a local immediate release analgesic at or near the damaged disc that provides pain relief so the procedure can be performed. If more pain control is needed, the patient can receive local delivery of a sustain release analgesic agent that can provide pain relief for extended periods of time (e.g., greater than 24 hours).

The depot can be designed to provide the desired release rate profile for immediate release and/or sustained release of the analgesic. The phrase "release rate profile" refers to the percentage of active ingredient that is released over fixed units of time, e.g., mcg/hr, mcg/day, mg/hr, mg/day, 10% per day for ten days, and the like. As persons of ordinary skill know, a release rate profile may be but need not be linear. By way of a non-limiting example, the drug depot may be a pellet that releases at least one analgesic agent in a bolus dose and at least one anti-inflammatory agent over a period of time.

The depot can be biodegradable. The term "biodegradable" includes that all or parts of the drug depot will degrade over time by the action of enzymes, by hydrolytic action and/or by other similar mechanisms in the human body. In various embodiments, "biodegradable" includes that the depot can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The depot may comprise non-biodegradable material. Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this invention, appear to be non-resorbable over the time frame of the use of the material for this invention.

The analgesic can provide the appropriate pain management medication. The phrase "pain management medication" includes one or more therapeutic agents that are administered to prevent, alleviate or remove pain entirely. These include anti-inflammatory agents, analgesics, anesthetics, narcotics, and so forth, and combinations thereof.

In various embodiments, the depot can be designed to cause an initial burst dose of one or more therapeutic agents within the first 24 hours after implantation. "Initial burst" or "burst effect" or "bolus dose" or "pulse dose" refer to the release of therapeutic agent from the depot during the first 24 hours after the depot comes in contact with an aqueous fluid (e.g., synovial fluid, cerebral spinal fluid, etc.). The burst effect may be an immediate release. The "burst effect" is believed to be due to the increased release of therapeutic agent from the depot. The initial burst effect or bolus dose may be determined beforehand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region or depot, in various embodiments, can be designed so that a larger initial dose may be released over a short period of time to achieve the desired effect. For example, if a drug depot is designed to release 15 mg of morphine per 48 hours, then the initial burst dose or bolus dose region or depot will be designed to release a percentage of the dose within the first 24 hours (e.g., 10 mg of morphine or 66% of the 48 hour dose within 24 hours). Thus, the burst effect of the drug depot or region releases more therapeutic agent than the sustained release region or depot.

A region or depot that utilizes a burst effect or bolus dose will release more therapeutic agent (e.g., analgesic and/or anti-inflammatory) than the sustained release region or depot. For example, particularly with painful conditions such as discogenic back pain, or the like, the initial burst effect of the drug depot or region of the drug depot will be advantageous as it will provide more immediate pain and/or inflammation relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, %56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the daily dose within the first one to twelve hours to reduce, prevent or treat pain and/or inflammation.

In some embodiments, the drug depot may have an initial burst effect to release the drug shortly after it is implanted. Various factors can be adjusted to achieve the initial burst of therapeutic agent release. First, the initial burst can be controlled by factors related to the property of the depot, such as the water immiscibility of the solvent, polymer/solvent ratio, and the property of the polymer. The extent of water immiscibility of the solvent used in the depot affects that rate aqueous body fluid can penetrate the depot to release the therapeutic agent. Generally, higher water solubility leads to a higher initial burst while water immiscibility leads to a lower initial burst or slower release (sustained release) of the therapeutic agent.

Suitable solvents that can be used to control initial burst release or sustained release include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, water, alcohol, low molecular weight PEG (less than 1,000 MW), triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethylsulfoxide, oleic acid, 1-dodecylazacyclo-heptan-2-one, or mixtures thereof. The solvent can be mixed, in various embodiments, with the therapeutic agent and/or polymers to obtain the desired release profile.

The depot may have pore forming agents, which include biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers. Such materials may be present in amounts varying from about 0.1% to about 100% of the weight of the polymer, but will typically be less than 50% and more typically less than 10-20% of the weight of polymer.

Further, varying the molecular weight of the polymer in the depot, or adjusting the molecular weight distribution of the polymer material in the depot vehicle can affect the initial burst and the release rate of therapeutic agent from the depot. Generally, a higher molecular weight polymer renders a lower initial burst and slower release rate of the therapeutic agent. The polymers may have different end groups such as acid and ester end groups. As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

Factors such as the particle size, the disintegration of the particulates, the morphology of the particulates (e.g., whether pores are present in the particulates before implanting or can be formed easily by body fluid attack), coatings, complex formation by the therapeutic agent and the strength of complex bond, can be manipulated to achieve the desired low initial burst and release rate.

The drug depot may comprise at least one analgesic agent or its pharmaceutically acceptable salt. Examples of analgesic agents include but are not limited to acetaminophen, a local anesthetic, such as for example, lidocaine, bupivacaine, ropivacaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propoxyphene, sufentanil, tilidine, tramadol or a combination thereof. Analgesic agents also include those with analgesic and anti-inflammatory properties, such as, for example, amitriptyline, carbamazepine, gabapentin, pregabalin, clonidine, or a combination thereof.

In some embodiments, the drug depot contains anti-inflammatory agents and/or analgesic comprising flurbiprofen, indoprofen, naproxol, pentazocine, proxazole, tramadol, verilopam, volazocine, xylazine, zucapsaicin, phenyhydantoin, phenobarbital, primidone, ethosuximide, methsuximide, phensuximide, trimethadione, diazepam, benzodiazepines, phenacemide, pheneturide, acetazolamide, sulthiame, bromide, nalorphine, naloxone, naltrexone, salycilates, phenylbutazone, indomethacin, phenacetin, dextropropoxyphene, levomethadyl, pethidine, remifentanil, flupirtine or a combination thereof.

In some embodiments, the anti-inflammatory and/or analgesic agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone, protein inhibitors of TNF, such as etanercept, Remicade, IL-1, such as Kineret®, p38, RANK, RANKL or a combination thereof.

The drug depot can comprise at least one analgesic agent or its pharmaceutically acceptable salt and/or at least one anti-inflammatory agent or its pharmaceutically acceptable salt may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one analgesic agent or its pharmaceutically acceptable salt and at least one anti-inflammatory agent or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered with the anti-inflammatory agent or analgesic agent include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dilhiocarbamate.

Specific examples of additional therapeutic agents suitable for use include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

For each of analgesic agent or anti-inflammatory agent, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or longer.

The drug depot may also be administered with non-active ingredients. These non-active ingredients may have multifunctional purposes including the carrying, stabilizing and controlling the release of the therapeutic agent(s). The sustained release process, for example, may be by a solution-diffusion mechanism or it may be governed by an erosion-sustained process.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation of the drug depot can occur either at the surface (heterogeneous or surface erosion) or uniformly throughout the drug depot (homogeneous or bulk erosion).

In various embodiments, the depot may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG). poly(propylene fumarate), conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, D,L-lactide-$\epsilon$-caprolactone, D,L-lactide-glycolide-$\epsilon$-caprolactone, poly(glycolide-$\epsilon$-caprolactone), $\epsilon$-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations or copolymers thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dI/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly (orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the analgesic and the anti-inflammatory are the only components of the pharmaceutical formulation.

In some embodiments, at least 75% of the particles in the depot have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area, in various embodiments, the depot may comprise sterile preservative free material.

The depot can be different sizes, shapes and configurations, such as for example, strip, rod, sheet, mesh, or the like. There are several factors that can be taken into consideration in determining the size, shape and configuration of the drug depot. For example, both the size and shape may allow for ease in positioning the drug depot at the target tissue site that is selected as the implantation site. In addition, the shape and size of the system should be selected so as to minimize or prevent the drug depot from moving after implantation or injection. In various embodiments, the drug depot can be shaped like a pellet, a sphere, a cylinder such as a rod, a flat surface such as a disc, film or sheet, strip, rod, mesh, or the like. Flexibility may be a consideration so as to facilitate placement of the drug depot. In various embodiments, the drug depot can be different sizes, for example, the drug depot may be a length of from about 2 to 4 cm and width of from about 1-2 cm and thickness of from about 0.25 to 1 mm, or length of from about 0.5 mm to 5 cm and have a diameter of from about 0.01 to about 2 mm. In various embodiments, the depot is a strip having dimensions of 2.5 cm×1.5 cm×0.5 mm. In various embodiments, the drug depot may have a layer thickness of from about 0.005 to 1.0 mm, such as, for example, from 0.05 to 0.75 mm.

Bulking or Sealing Agents

The analgesic is used in combination with a bulking or sealing agent. The term "bulking" as used herein refers to partially or fully bulking a tissue or partially or fully filling a biological cavity. The cavity can be preexisting or formed for the purpose of treatment. Bulking can be performed, for example, for reconstruction, augmentation, or replacement of body tissue including the intervertebral disc of the spine. For example, bulking agents can be used to restore, repair and/or rehydrate the nucleus pulposus and/or disc space by using a catheter that is pushed through the annulus fibrosis. Once inside the disc space or nucleus, the bulking agent or sealing agent is released and the material expands to fill the disc space as needed.

In some embodiments, the bulking or sealing agent can degrade. In other embodiments, the bulking or sealing agent may be a permanent or non-degrading implant, but have appropriate porosity to allow influx of fluid and nutrients without its structure being altered. This porosity may be present upon implantation or develop over time by dissolution of a porogen. The bulking or sealing agent may be responsive to enzymes within the body or within its formulation to modulate the degradation or porosity of the material. Alternatively the bulking or sealing agent could contain magnetic particles which would agitate the material and allow influx of nutrients, cells, growth factors, etc. for healing and metabolism.

The term "sealing" as used herein refers to partially or fully covering a tissue or cell with the agent. Sealing can be performed, for example, for adhesion prevention, to promote adhesion between surfaces, or for tissue or cellular encapsulation. For example, a damaged intervertebral disc can be sealed to prevent or reduce the nucleus pulposus from leaking out of the annulus fibrosis by using a sealing agent in the damaged area around the annulus fibrosis.

A wide variety of biocompatible polymeric materials may be used as the bulking agent and/or sealing agent, including, but not limited to, silicon, polyurethane, copolymers of silicon and polyurethane, polyolefins, such as polyisobutylene and polyisoprene, neoprene, nitrile, polyvinyl alcohol, acrylamides such as polyacrylic acid and poly(acrylonitrile-acrylic acid), non-biologically absorbable polyurethanes, polyethylene glycol, poly(N-vinyl-2-pyrrolidone), acrylates such as polyacrylates, poly(-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, glycosaminoglycans, collagen, polyethylene oxide, co-polymers of PVA and PVP, and combinations thereof. The hydrogel materials may further be cross-linked to provide further strength. Examples of polyurethanes include thermoplastic polyurethanes, aliphatic polyurethanes, segmented polyurethanes, hydrophilic polyurethanes, polyether-urethane, polycarbonate-urethane and silicon polyether-urethane. Other suitable hydrophilic polymers include naturally-occurring materials such as glucomannan gel, polyphosphazenes, hyaluronic acid, polysaccharides, such as cross-linked carboxyl-containing polysaccharides, alkyl celluloses, hydroxyalkyl methyl celluloses, sodium chondroitin sulfate, cyclodextrin, polydextrose, dextran, gelatin, guar gum, gellan gum, pectin, lecithin, and combinations thereof. Other suitable examples of biologically acceptable polymers include biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. One can also use superabsorbent polymers (SAP) with or without additives. Superabsorbent polymers may include polymer chains that are synthetic, natural, and hybrid synthetic/natural polymers. Exemplary superabsorbent polymers may include, but are not limited to, polyacrylic acid, polymethacrylic acid, polymaleic acid, copolymers thereof, and alkali metal and ammonium salts thereof; graft copolymers of starch and acrylic acid, starch and saponified acrylonitrile, starch and saponified ethyl acrylate, and acrylate-vinyl acetate copolymers saponified; polyvinylpyrrolidone, polyvinyl alkylether, polyethylene oxide, polyacrylamide, and copolymers thereof; copolymers of maleic anhydride and alkyl vinylethers; saponified starch graft copolymers of acrylonitrile, acrylate esters, vinyl acetate, and starch graft copolymers of acrylic acid, methyacrylic acid, and maleic acid; the product of crosslinking acrylamide with backbones of kappa-carrageenan and soldium alginate using methylenebisacrylamide and potassium persulfate; and the product of crosslinking, using a bifunctional crosslinking reagent, an acyl-modified protein matrix such as soy protein isolate which has been acyl-modified by treatment with ethylenediaminetetraacetic acid dianhydride; mixtures and combinations thereof. Further, one can use silicon-based materials, polyethylene terephthalate, polycarbonate, thermoplastic elastomers and copolymers such as ether-ketone polymers such as poly etheretherketone or a combination thereof.

In some embodiments, the bulking and/or sealing agent may be made of or can include any hydrostatic and/or hemostatic agents for sealing, (e.g., gelfoam), tissues, and/or proteins including collagen. These agents may be derived from allograft or xenograft tissue or be synthetic in nature.

In some embodiments, the bulking and/or sealing agent can be a superabsorbent polymer (SAP) that is capable of absorbing fluids in an amount that is at least ten, twenty, or twenty-five times the weight of the SAP in its dry form. The fluid is taken into the molecular structure of the superabsorbent polymer and not simply contained in pores from which it can be expressed by squeezing. As the SAP absorbs water, it will expand and provide the appropriate bulking characteristic or sealing characteristics to the damaged vertebrae.

The SAP can be cross-linked to enhance its absorbency capacity and gel strength. SAPs useful in some embodiments described herein have adequately high sorption capacity, and relatively low gel strength compared to the hydrogels used in nucleus and intervertebral disc replacement devices. Gel strength relates to the tendency of the swollen polymer to deform under an applied stress. A low gel strength may be desirable because the retained, or original, nucleus pulposus and annulus fibrosis of the intervertebral disc may be intended to provide the majority of the strength in the intervertebral disc. The superabsorbent polymers, in comparison, may be intended to offer little or no structural strength to the intervertebral disc, other than that provided by the SAPs' ability to rehydrate the disc and the bulking effect of introducing the SAPs to the disc space.

In some embodiments, the superabsorbent polymers are no more than about 30%, or 20%, or 10% crosslinked. In another embodiment, the superabsorbent polymers are not more than about 20% crosslinked. In these embodiments, the relatively low percentage of crosslinked polymer chains ensures that the superabsorbent polymers are weak and do not provide substantial mechanical strength to the intervertebral disc, other than the strength provided by the SAPs' ability to absorb fluids and rehydrate the disc space. Additionally, the low crosslinking of the superabsorbent polymers helps to ensure that the polymers are able to expand and absorb large amounts of water.

Superabsorbent polymers may include polymer chains that are synthetic, natural, and hybrid synthetic-natural polymers. Natural polymers include polysaccharides such as cellulose, starch, and regenerated cellulose that are modified to be carboxylated, phosphonoalkylated, sulphoxylated or phosphorylated, thereby causing the polymer chains to become highly hydrophilic. Synthetic polymers that can be used as SAP include, but are not limited to, polyacrylates. U.S. Pat. No. 5,147,343, U.S. Pat. No. 4,673,402, U.S. Pat. No. 5,281,207, and U.S. Pat. No. 4,834,735 disclose many types of SAPs and methods for making them, and are incorporated herein by reference in their entirety in accordance with the described embodiments.

Because the superabsorbent polymers act to attract and maintain water in the disc space, and thereby rehydrate the nucleus pulposus, it is desirable that healthy annulus fibrosis and endplates be present in the intervertebral disc. Otherwise, delivery of a superabsorbent polymer to the intervertebral disc may not result in the desired level of rehydration and augmentation. In particular, a compromised annulus fibrosis or endplate may not be capable of retaining the water that is attracted to the superabsorbent polymer, the superabsorbent polymer itself, and the nucleus tissue. Therefore, in the case of a significantly compromised annulus fibrosis or endplate, little or no rehydration of the nucleus may occur even after introduction of a superabsorbent polymer to the disc space.

In some embodiments, the methods provided can be used to treat patients with mild to moderate disc degeneration and an essentially intact and competent annulus fibrosis. As explained herein, delivery of the superabsorbent polymers may be accomplished with little or no additional injury to the annulus fibrosis. In some embodiments, the methods provided herein may be especially useful for patients that are not good candidates for nucleus replacement surgery, spinal fixation, total disc replacement, spinal fusion, and other surgical regimens for the treatment of degenerated intervertebral discs.

Accordingly, in some embodiments, there is a method for treating an intervertebral disc having a nucleus pulposus and an annulus fibrosis, using one or more bulking and/or sealing agents. The method comprises introducing the bulking and/or sealing agent (e.g., SAP) into the intervertebral disc space without removing nucleus pulposus or annulus fibrosis material, thereby rehydrating the intervertebral disc. The intervertebral disc may be a cervical, lumbar, or thoracic disc.

In some embodiments, there is a method for bulking up an intervertebral disc having a nucleus pulposus and an annulus fibrosis, using one or more bulking and/or sealing agent. The method comprises introducing the bulking and/or sealing agent into the intervertebral disc space without removing nucleus pulposus or annulus fibrosis material, thereby increasing the height, the volume, and/or the intra-discal pressure of the disc. The intervertebral disc may be a cervical, lumbar, or thoracic disc.

In some embodiments, provided herein, the method is used to rehydrate the intervertebral disc until equilibrium swelling is attained. Additionally, the methods may be useful to treat an intervertebral disc that already has at least partially collapsed. The amount of bulking and/or sealing agents placed in the intervertebral disc is sufficient to increase the disc height, and/or restore the disc's natural height. A skilled artisan will be capable of determining the desired amount of bulking and/or sealing agents based on a number of factors, including, for example, the degree of disc degeneration, the age, weight, and health of the patient, and the degree of restoration required. Additionally, the methods provided herein may be used to slow the rate of progressive collapse of an intervertebral disc and/or maintain the height of an intervertebral disc experiencing progressive collapse.

In some embodiments, suitable bulking and/or sealing agents that can be used in the methods of the present application to help reduce and/or prevent pain and/or inflammation include crosslinkable macromonomers that form hydrogels. These bulking and/or sealing agents macromers have a backbone of a polymer having units with a 1,2-diol and/or 1,3-diol structure. Such polymers include poly(vinyl alcohol) (PVA) and hydrolyzed copolymers of vinyl acetate, for example, copolymers with vinyl chloride, N-vinylpyrrolidone, etc. The backbone polymer may contain pendant chains bearing crosslinkable groups and, optionally, other modifiers. When crosslinked, the macromers form hydrogels advantageous for use as bulking and/or sealing agent for different tissue types. Specific examples of bulking and/or sealing agents include microspheres formed from macromers, wherein the macromers prior to crosslinking have a polymeric backbone comprising units with a 1,2-diol or 1,3-diol structure and at least two pendant chains bearing crosslinkable groups which are olefinically unsaturated groups, wherein the macromers are crosslinked via free radical polymerization to form a hydrogel. These types of polymeric bulking and/or sealing agents are described in U.S. Pat. No. 6,652,883 and U.S. Pat. No. 7,070,809, assigned to BioCure, Inc. The entire disclosures of these patents are incorporated by reference herein.

Suitable bulking and/or sealing agents can be part of a prosthetic nucleus pulposus that is implanted at or near the damaged site to repair or replace a damaged disc. These agents include a hydrogel formed from a macromer having a polymeric backbone comprising units with a 1,2-diol or 1,3-diol structure and at least two pendant chains bearing crosslinkable groups and an amphiphilic comonomer. Hydrogels include a material having an aqueous phase with an interlaced polymeric component, with at least 10% to 90% of its weight as water. The hydrogel can have a yield load between about 1000 to 6000 Newtons or a compression modulus of approximately 3 mega pascals at 10-30% strain and the comonomer can be diacetone acrylamide (DAA), N-vinyl caprolactam, N-(butoxymethyl)acrylamide, N-acroyl morpholine, crotonamide, N,N-dimethyl acrylamide, N-octadecylacrylamide, acrylamide or a combination thereof. The hydrogel can have a macromer having a poly (vinyl alcohol) backbone with a molecular weight of about 14,000 and the pendant chains bearing crosslinkable groups are N-acrylamidoacetaldehyde dimethyl acetal (NAAADA) in an amount of about 6 to 21 crosslinkers per PVA. These types of polymeric bulking and/or sealing agents are described in U.S. Ser. No. 11,170,915, filed Jun. 29, 2005 and published as US 2005/0288789 assigned to BioCure, Inc. The entire disclosure of this patent application is incorporated by reference herein.

Suitable bulking and/or sealing agents can comprise macromers having a backbone comprising a polymeric backbone having units with a 1,2-diol or 1,3-diol structure, such as polyvinyl alcohol, and pendant chains bearing crosslinkable groups and, optionally, other modifiers. When crosslinked, the macromers form hydrogels that can seal and fill lumens and spaces, such as in an intervertebral disc. In some embodiments, the bulking and/or sealing agent can be crosslinked and form microspheres. In some embodiments, the polymeric backbone comprises a polyhydroxy polymer and the pendant chains bearing crosslinkable groups are attached to the backbone via the 1,2-diol or 1,3-diol groups. In some embodiments, the pendant chains bearing crosslinkable groups are attached to the backbone via cyclic acetal linkages. These types of polymeric bulking and/or sealing agents are described in U.S. Pat. No. 6,676,971, and U.S. Pat. No. 6,710,126, assigned to BioCure, Inc. These entire disclosures of these patents are incorporated by reference herein.

Suitable bulking and/or sealing agents can comprise polymerizable carbohydrate esters and polymers therefrom and homo- and co-polymers having monomers with hydrophilic, amphiphilic or hydrophobic properties that are able to form hydrogels, as described in U.S. Pat. No. 5,571,882. The entire disclosure of this patent is incorporated by reference herein.

Suitable bulking and/or sealing agents can include membranes made from amphiphilic copolymers. The amphiphilic copolymers can be ABA copolymers, where one of A and B is hydrophilic and the other is hydrophobic. The copolymers may be crosslinked to form more stable structures. Crosslinking can be accomplished using a variety of methods, including end to end polymerization of copolymers having terminal unsaturated groups as described in U.S. Pat. No. 6,723,814. The entire disclosure of this patent is incorporated by reference herein.

Suitable bulking and/or sealing agents can be sprayed on in situ at or near the damaged tissue and then gel in situ to form a hydrogel. These bulking and/or sealing agents include macromers having water soluble regions and crosslinkable regions as described in U.S. Ser. No. 09/960,449, filed Sep. 21, 2001 and published as US 2002/0122771. This entire disclosure of this patent application is incorporated by reference herein. The bulking or sealing agent may react with the tissue within the intervertebral disc to ionically or covalently bond to the tissue, thereby enhancing the integration of the material.

The bulking and/or sealing agents or even the drug can be incorporated into polymeric hollow particles for delivery that change permeability in response to a change in an external stimulus such as pH, temperature, light, ionic strength, electric field, magnetic field and/or solvent composition. The hollow particles can have a shell formed of an amphiphilic triblock ABA or BAB copolymer, where A is a hydrophilic block and B is a hydrophobic block. Low permeability particles with a reversibly permeable shell expand and increase permeability in response to a stimulus so that an active agent such as a therapeutic, prophylactic or diagnostic agent can be introduced. Removing the stimulus allows the particles to return to a low permeability state to form particles loaded with the active agent. Surfaces of the particles can be modified with specific ligands that allow the particles to be directed to a specific target via molecular recognition as described in U.S. Pat. No. 6,616,946, assigned to BioCure, Inc. The entire disclosure of this patent is incorporated by reference herein.

The bulking agent and/or sealing agent can be incorporated in a syringe or cannula and delivered to the intervertebral disc. The bulking and/or sealing agent may be delivered to the disc space in a variety of forms, such as beads, fibers, flakes, granules, microspheres, nano-particles, particles, pellets, platelets, powder, randomly shaped particles, rods, chunks, pieces, and so forth.

In some embodiments, whatever form the bulking and/or sealing agent is in, it may be delivered to the intervertebral disc space, for example, utilizing "dry" or "wet" delivery methods.

In the "wet" delivery method, the bulking and/or sealing agent may be fluidized, for example, by mixing the superabsorbent polymers with a medium to form a gel, suspension, paste, solution, mixture, etc. of the bulking and/or sealing agent that is sufficiently fluid to be delivered through a needle, catheter, trocar, cannula, syringe, caulk gun-like device, barrel-plunger device, other injection or extrusion devices, or any other such applicable delivery device. For example, the delivery device may be used to pierce or puncture the annulus fibrosis in order to reach the interior of the disc space and nucleus pulposus. If desired, a more rigid, larger diameter cannula may be used to gain access to the outer disc annulus, and a smaller diameter needle may be used to puncture the annulus and inject the superabsorbent polymer into the disc space. Additionally, if desired, a more rigid instrument such as a stylet may be used to guide the delivery device through the body and towards the disc space.

In some embodiments, the flowable bulking and/or sealing agent may be introduced into the delivery device and subjected to pressure or mechanical forces in order to force the bulking and/or sealing agent to exit the distal end of the delivery device and enter the intervertebral disc space. In an exemplary embodiment, a syringe filled with the superabsorbent polymer in the form of a gel, suspension, paste, solution, mixture, etc. may be used to force the bulking and/or sealing agent through the delivery device (e.g., a needle, cannula, catheter, trocar, etc.) and into the disc space.

In some embodiments, the bulking and/or sealing agent may be delivered to the disc space via a "dry" delivery method, without rendering the bulking and/or sealing agent flowable. According to the dry delivery method, the superabsorbent materials may be packed into a small diameter delivery device such as a needle, catheter, trocar, cannula, etc. in the form of a dry powder, particulates, small chunks, pellets, short rods, chunks, pieces, and so forth. No fluid is mixed with the superabsorbent materials prior to delivery to the intervertebral disc space. In some embodiments, the delivery device has a diameter of no more than about 3 mm, 2 mm, or 1 mm.

In some embodiments, the annulus fibrosis may be punctured and the delivery device inserted. In some embodiments, the delivery device itself may be used to puncture the annulus fibrosis, especially when the delivery device is a needle or trocar. The distal end of the delivery device then may be brought close to the center of the disc space. A plunger, stylet, or other such device may be used to extrude or push the dry bulking and/or sealing agent material through the delivery device and into the disc space. When sufficient bulking and/or sealing agent material has been delivered to the disc space, the delivery device may be removed.

Cannula or Needle

The drug, drug depot, bulking agent and/or sealing agent can be loaded in a cannula or needle that is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments, the plunger, cannula, drug, drug depot, bulking agent and/or sealing agent can include markings that indicate location at or near the site beneath the skin. Radiographic markers can be included to permit the user to accurately position the drug, drug depot, bulking agent and/or sealing agent into the site of the patient. These radiographic markers will also permit the user to track movement and degradation of the drug, drug depot, bulking agent and/or sealing agent at the site over time. In this embodiment, the user may accurately position the drug, drug depot, bulking agent and/or sealing agent in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography. The bulking or sealing agent may be administered in conjunction with a standard discogram.

In one embodiment, the delivery system for the bulking agent and/or sealing agent and the analgesic can include any syringe based system that would be used to administer a discogram. These syringe based systems include inflation syringes with a fine and coarse drive, in conjunction with a pressure gage.

In one embodiment, the bulking agent and/or sealing agent and the analgesic can be administered to the disc using a Kyphon Discyphor catheter system available from Kyphon, Inc. in Sunnyvale, Calif., USA, where the damaged disc can be diagnosed and treated using the same catheter. Thus, the analgesic and the bulking agent or sealing agent can be delivered to the disc in one procedure using the same catheter system.

Administration

In various embodiments, an immediate release analgesic and/or anti-inflammatory followed by a sustained release analgesic and/or anti-inflammatory is administered locally at or near an intervertebral to reduce or prevent pain. In various embodiments, the analgesic may be parenterally administered. The term "parenteral" as used herein refers to modes of administration, which bypass the gastrointestinal tract, and include for example, intramuscular, intraperitoneal, intrasternal, subcutaneous, intra-operatively, intrathecally, intradiskally, peridiskally, epidurally, perispinally, intraarticular or combinations thereof. Administration may be performed while the patient is at rest or in a distracted position, while standing, laying or sitting.

In various embodiments, because the combination of analgesic and/or anti-inflammatory agent is locally administered, therapeutically effective doses may be less than doses administered by other routes (oral, topical, etc.). In turn, systemic side effects, such as for example, liver transaminase elevations, hepatitis, liver failure, myopathy, constipation, etc. may be reduced or eliminated. Because the local analgesic and/or anti-inflammatory is administered before any therapeutic and/or diagnostic procedure is performed, the patient does not experience pain or the pain from the procedure is reduced. After the procedure, a sustained release analgesic and/or anti-inflammatory is administered to insure proper pain management.

The analgesic and/or anti-inflammatory can be delivered to any site beneath the skin, including, but not limited to, at least one muscle, ligament, tendon, cartilage, spinal disc, spinal foraminal space, near the spinal nerve root, or spinal canal.

In some embodiments, a method of augmenting a nucleus pulposus within an annulus fibrosis in a patient in need of such treatment is provided, the method comprising administering an immediate release analgesic at or near the annulus fibrosis; administering a bulking agent or sealing agent in the nucleus pulposus; and administering a sustained release analgesic within the annulus fibrosis or nucleus pulposus, wherein the sustained release analgesic releases the analgesic over a period of at least one day.

A vertebral joint section or a motion segment of a vertebral column includes adjacent vertebral bodies. The vertebral bodies include endplates. An intervertebral disc space is located between the endplates and an annulus fibrosis surrounds the space and holds a nucleus pulposus.

In another embodiment, an annular tear is present that the nucleus pulposus can herniate out of this tear. In the embodiments of the present application, a local analgesic agent is delivered next to the annulus fibrosis of the disc and next to the tear by inserting a cannula into the patient and locating the cannula at or near the annulus and delivering the immediate release analgesic to the target tissue site. The analgesic agent can be delivered by coupling a syringe containing this agent to a port. The analgesic will be an immediate release formulation (e.g., liquid, powder, depot, etc.) that will provide immediate relief to the patient of the pain so that further procedures can be performed.

In another embodiment, an annular tear is present and the nucleus pulposus has left the disc space from this tear. Therefore, the disc has a space that needs repair using a bulking agent. In the embodiments of the present application, a bulking agent is delivered to the nucleus pulposus by introducing a catheter into the tear in the annulus fibrosis and delivering the bulking agent in to the depleted nucleus pulposus space. The bulking agent will bulk up, or supplement the nucleus pulposus to the annulus edge. The bulking agent can be delivered to the disc space by coupling a syringe containing the bulking agent to a port and injecting it into the target tissue site. In some embodiments, the bulking agent will polymerize and/or cure in situ. This procedure is performed to the disc after a local immediate release analgesic is given to the patient. After a bulking agent has been administered at or near, or in the site, a sustained release analgesic agent (e.g., drug depot) is administered in the annulus fibrosis of the disc and next to the tear by inserting a cannula into the patient and locating the cannula through the annulus by a hole (the hole can be created by the practitioner) and delivering the sustained release analgesic to the target tissue site. The analgesic will be a sustained release formulation (e.g., liquid, powder, depot, etc.) that will provide long term relief to the patient of the pain. In this embodiment, the nucleus is accessed using a posterior bilateral approach. In alternative embodiments, the annulus may be accessed with a lateral approach, an anterior approach, a trans-pedicular/vertebral endplate approach or any other suitable nucleus accessing approach. Although a bilateral approach is described, a unilateral or multi-lateral approach may be suitable.

In another embodiment, an annular tear is present and the nucleus pulposus has left the disc space from this tear. Therefore, the disc has a space that needs repair using a bulking agent. In the embodiments of the present application, a bulking agent is delivered to the nucleus pulposus by introducing a catheter into the tear at in the annulus fibrosis and delivering the bulking agent in to the depleted nucleus pulposus space. The bulking agent will bulk up the nucleus pulposus. The bulking agent can be delivered to the disc space by coupling a syringe containing the bulking agent to port and injecting the bulking agent into the target tissue site. This procedure is performed to the disc after a local immediate release analgesic is given to the patient. After a bulking agent has been administered at or near or in the site, a sustained release analgesic agent (e.g., drug depot) is administered to the annulus fibrosis at a region adjacent to it that is next to the tear by inserting a cannula into the patient and locating the cannula next to the annulus and delivering the sustained release analgesic to the target tissue site. The analgesic will be a sustained release formulation (e.g., liquid, powder, depot, etc.) that will provide long term relief to the patient of the pain.

In some embodiments, the therapeutically effective dosage amount and the release rate profile of the analgesic and/or anti-inflammatory agent are sufficient to reduce inflammation and/or pain for a period of at least one day, for example, 1-90 days, 1-10 days, 1-3 days, 3-7 days, 3-12 days; 3-14 days, 3-45 days, 7-10 days, 7-14 days, 7-21 days, 7-30 days, 7-50 days, 7-90 days, 7-140 days, or 14-140 days.

In some embodiments, the at least one analgesic agent and at least one anti-inflammatory agent or a portion of the at least one analgesic agent and at least one anti-inflammatory agent are administered as a bolus dose at the target tissue to provide an immediate release of the at least one analgesic agent and at least one anti-inflammatory agent.

In some embodiments, there is a composition useful for the treatment of inflammation comprising an effective amount of at least one analgesic agent and at least one anti-inflammatory agent that is capable of being administered to e.g., a pain or inflammatory site. By way of example, they may be administered locally to the foraminal spine, paraspinal muscles or subcutaneous tissues.

In some embodiments, a plurality of depots containing the analgesic and/or anti-inflammatory agent can be placed around the disc to provide a strategy to triangulate around the pain generator. A strategy of triangulation may be effective when administering multiple depot pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations. Alternatively repeat administration to lengthen the delivery timeframe may be required.

In some embodiments, the drug depot is implantable at or near a target tissue site at the time of surgery. The active ingredients may then be released from the depot via diffusion in a sustained fashion over a period of time, e.g., 1-3 days, 3-15 days, 5-10 days or 7-10 days post surgery in order to address pain and inflammation.

In some embodiments, a desired release rate profile is maintained for at least three days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days.

In some embodiments, the drug depot may release 5%, 10%, 15%, 20%, 25%, 30%, 40%, 50%, 60%, 70%, 80%, 90%, 95%, or 99% of the at least one analgesic agent or pharmaceutically acceptable salt thereof and at least one anti-inflammatory agent or pharmaceutically acceptable salt thereof relative to a total amount of at least one analgesic agent or pharmaceutically acceptable salt thereof and at least one anti-inflammatory agent loaded in the drug depot over a period of at least three days, at least seven days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days. In various embodiments, the analgesic will be released in an initial burst dose, then the analgesic will be released daily for 3 days and then stop (e.g., this will be suitable to reduce, prevent or treat, post-operative pain), while the anti-inflammatory agent will be released daily without a burst dose for 3 to 12 days, 5 to 10 days or 7 to 10 days after the drug depot is administered to the target tissue site.

In various embodiments, a kit is provided comprising one or more drug depots (containing the immediate release and/or sustained release analgesic), the bulking agent and/or sealing agent. The kit may include additional parts along with the drug depot and/or medical device combined together to be used to implant the drug depots (e.g., pellets, strips, meshes etc.). The kit may include the drug depot delivery device in a first compartment. The second compartment may include a canister holding the drug depots and any other instruments needed for the localized drug delivery. A third compartment may include gloves, drapes, needles, wound dressings and other procedural supplies for maintaining sterility of the implanting process, as well as an instruction booklet. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Method of Making Drug Depot

In various embodiments, the drug depot comprising the active ingredients can be made by combining a biocompatible polymer and a therapeutically effective amount of the active ingredients or pharmaceutically acceptable salts thereof and forming the implantable drug depot from the combination.

Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where water-soluble therapeutic agents are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. Thus, a sustained release region of the drug depot may, in various embodiments, be made by immediately removal of water or moisture.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also comprise combining a biocompatible polymer and a therapeutically effective amount of at least one analgesic agent or pharmaceutically acceptable salt thereof and at least one anti-inflammatory agent or pharmaceutically acceptable salt thereof and forming the implantable drug depot from the combination.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of treating pain from an intervertebral disc in a patient in need of such treatment, the method comprising:
   administering an immediate release analgesic at or near the intervertebral disc;
   administering a bulking agent to at least partially bulk a tissue or fill a biological cavity after administering the immediate release analgesic, the bulking agent remaining as a permanent or non-degrading implant, the bulking agent comprising a macromer having a polyvinylalcohol backbone comprising units with a 1,2-diol structure and at least two pendent chains bearing crosslinkable groups, the bulking agent further comprising an amphiphilic comonomer, wherein the implant has a yield load between 1000 to 6000 Newtons to facilitate replacement of a nucleus pulpous; and
   administering a sustained release analgesic within the intervertebral disc after administering the bulking agent, wherein the sustained release analgesic releases the analgesic over a period of at least one day.

2. A method according to claim 1, wherein the sustained release analgesic is released over a period between 3 days to 45 days to treat the pain from the intervertebral disc.

3. A method according to claim 1, wherein the bulking agent comprises a biocompatible material that is curable in-situ in the intervertebral disc.

4. A method according to claim 1, wherein the bulking agent is polymerizable in-situ in the intervertebral disc.

5. A method according to claim 1, wherein the sustained release analgesic is in a drug depot comprising a polymer comprising poly (lactide-co-glycolide) (PLGA), polylactide (PLA), polyglycolide (PGA), D-lactide, D,L-lactide, L-lactide, D,L-lactide-caprolactone, D,L-lactide-glycolide-caprolactone or a combination thereof.

6. A method according to claim 1, wherein the bulking agent is administered by passing through an opening in an annulus fibrosus to supplement the nucleus pulposus or delivering the bulking agent through an opening in a pedicle to adjacent vertebrae.

7. A method according to claim 1, wherein administering the bulking agent comprises administering the bulking agent until the intervertebral disc is rehydrated and equilibrium swelling is attained.

8. A method according to claim 1, wherein administering the bulking agent comprises administering the bulking agent such that the intervertebral disc moves from a collapsed height to an increased height that is equal to the intervertebral disc's natural height.

9. A method according to claim 1, wherein the intervertebral disc is exhibiting progressive disc collapse, and administering the bulking agent comprises administering the bulking agent until the rate of disc collapse decreases.

10. A method according to claim 1, wherein the comonomer of the bulking agent is selected from a group consisting of diacetone acrylamide (DAA), N-vinyl caprolactam, N-(butoxymethyl)acrylamide, N-acroyl morpholine, crotonamide, N,N-dimethyl acrylamide, N-octadecylacrylamide and acrylamide.

11. A method according to claim 1, wherein the macromer has a molecular weight of about 14,000.

12. A method according to claim 1, wherein the pendent chains bearing crosslinkable groups are N-acrylamidoacetaldehyde dimethyl acetal.

13. A method according to claim 12, wherein the pendent chains bearing crosslinkable groups are present in an amount of about 6 to 21 per polyvinylalcohol.

14. A method of treating pain from an intervertebral disc in a patient in need of such treatment, the method comprising:
    administering an immediate release analgesic at or near the intervertebral disc;
    administering a bulking agent to at least partially bulk a tissue or fill a biological cavity after administering the immediate release analgesic, the bulking agent remaining as a permanent or non-degrading implant, the bulking agent comprising a macromer having a polyvinylalcohol backbone comprising units with a 1,3-diol structure and at least two pendent chains bearing crosslinkable groups, the bulking agent further comprising an amphiphilic comonomer, wherein the implant has a yield load between 1000 to 6000 Newtons to facilitate replacement of a nucleus pulpous; and
    administering a sustained release analgesic within the intervertebral disc after administering the bulking agent, wherein the sustained release analgesic releases the analgesic over a period of at least one day.

15. A method according to claim 14, wherein the comonomer of the bulking agent is selected from a group consisting of diacetone acrylamide (DAA), N-vinyl caprolactam, N-(butoxymethyl)acrylamide, N-acroyl morpholine, crotonamide, N,N-dimethyl acrylamide, N-octadecylacrylamide and acrylamide.

16. A method according to claim 14, wherein the macromer has a molecular weight of about 14,000.

17. A method according to claim 14, wherein the pendent chains bearing crosslinkable groups are N-acrylamidoacetaldehyde dimethyl acetal.

18. A method according to claim 17, wherein the pendent chains bearing crosslinkable groups are present in an amount of about 6 to 21 per polyvinylalcohol.

19. A method according to claim 14, wherein the bulking agent is administered by passing through an opening in an annulus fibrosus to supplement the nucleus pulposus or delivering the bulking agent through an opening in a pedicle to adjacent vertebrae.

20. A method of treating pain from an intervertebral disc in a patient in need of such treatment, the method comprising:
    administering an immediate release analgesic at or near the intervertebral disc;
    administering a bulking agent to at least partially bulk a tissue or fill a biological cavity after administering the immediate release analgesic, the bulking agent remaining as a permanent or non-degrading implant, the bulking agent comprising a macromer having a polyvinylalcohol backbone with a 1,2-diol or 1,3-diol structure, a molecular weight of about 14,000 and pendent chains bearing N-acrylamidoacetaldehyde dimethyl acetal crosslinkable groups in an amount of about 6 to 21 per polyvinylalcohol, the bulking agent further comprising an amphiphilic comonomer selected from a group consisting of diacetone acrylamide (DAA), N-vinyl caprolactam, N-(butoxymethyl)acrylamide, N-acroyl morpholine, crotonamide, N,N-dimethyl acrylamide, N-octadecylacrylamide and acrylamide, wherein the implant has a yield load between 1000 to 6000 Newtons to facilitate replacement of a nucleus pulpous; and
    administering a sustained release analgesic within the intervertebral disc after administering the bulking agent, wherein the sustained release analgesic releases the analgesic over a period of at least one day.

* * * * *